United States Patent
Seawright (10) Patent No.: US 6,644,694 B2
(45) Date of Patent: Nov. 11, 2003

(54) WEARABLE FOLDED MAP

(76) Inventor: Phillip Seawright, P.O. Box 427, Hooker, OK (US) 73945

(*) Notice: Subject to any disclaimer, the term of this patent is extended or adjusted under 35 U.S.C. 154(b) by 0 days.

(21) Appl. No.: 10/189,271

(22) Filed: Jul. 1, 2002

(65) Prior Publication Data

US 2003/0006608 A1 Jan. 9, 2003

Related U.S. Application Data

(60) Provisional application No. 60/303,356, filed on Jul. 6, 2001.

(51) Int. Cl.$^7$ .............................. G09B 29/00; B42D 3/04
(52) U.S. Cl. ....................... 283/34; 2/16; 2/160; 2/170; 2/162; 2/312; 40/124.09; 40/191; 40/304; 40/586; 40/633; 40/665; 40/904; 206/39.7; 283/34; 283/106; 281/34; 281/115; 224/164; 224/165; 224/221; 224/222; 224/224; 224/219; 224/620; 224/650; 224/660; 224/901.4; 224/901.6; D11/3; D11/4; D11/62; D11/110; 428/64.1; 428/99
(58) Field of Search ..................... 40/124.09, 191, 40/304, 665, 586, 633, 904; D11/3, 4, 62, 110; 428/64.1, 99

(56) References Cited

U.S. PATENT DOCUMENTS

| | | | | |
|---|---|---|---|---|
| 3,660,916 A | * | 5/1972 | McDermott et al. | ........... 40/633 |
| 4,341,331 A | * | 7/1982 | McDougall | ................. 224/219 |
| 4,415,106 A | | 11/1983 | Connell et al. | |
| 4,536,889 A | * | 8/1985 | Taylor et al. | .................. 2/160 |
| D300,786 S | | 4/1989 | Josselyn | |
| 4,905,881 A | * | 3/1990 | Graber | ........................ 224/222 |
| 4,957,310 A | * | 9/1990 | Bissonnette | ................. 283/34 |
| 4,982,837 A | * | 1/1991 | Toth | .......................... 206/38.1 |
| 4,984,683 A | * | 1/1991 | Eller | ............................ 206/38 |
| D323,939 S | * | 2/1992 | Mok | ............................ D3/230 |
| 5,156,898 A | * | 10/1992 | McDonald | ...................... 281/5 |
| 5,170,917 A | * | 12/1992 | Tourigny | .................... 224/219 |
| 5,273,432 A | | 12/1993 | White | |
| 5,386,933 A | * | 2/1995 | Greene et al. | .............. 224/219 |
| 5,390,957 A | | 2/1995 | Metzler | |
| 5,400,936 A | | 3/1995 | Jones et al. | |
| 5,579,969 A | | 12/1996 | Brandell | |
| 5,588,571 A | * | 12/1996 | Mazzo | ........................ 224/222 |
| 5,671,481 A | * | 9/1997 | Giard | ............................. 2/170 |
| 5,685,095 A | | 11/1997 | DeMasi | |
| 5,725,252 A | | 3/1998 | Crum | |
| 5,732,978 A | | 3/1998 | Tunnell, IV | |
| 5,743,449 A | * | 4/1998 | McBride | ..................... 224/191 |

(List continued on next page.)

OTHER PUBLICATIONS

Bain, Ian, The Miura–Ori Map, http://www.worthhall.demon.co.uk/theory/miura.htm, Oct. 10, 1980.
Author/inventor unknown, Magnetic Phone Index, as seen at http://worldclasspromotions.com/misc–specials/phonelist–c.html, date of invention unknown, first publication unkown.

Primary Examiner—A. L. Wellington
Assistant Examiner—Mark T. Henderson (57) ABSTRACT

A foldable, weather-resistant reference guide for wearing on the arm, torso, or leg. The foldable, weather-resistant reference guide is attached to a soft, flexible keeping member that holds the reference guide in a folded configuration. The keeping member is connected to or comprised of at least one flexible strap such as an elastic strap that encircles the arm, torso, or leg. The reference guide itself is made of a synthetic fiber paper for weather-resistance. The reference guide folds-up when not in use and is held in place by the keeping member so that the reference guide does not interfere with any physical activities such as snow skiing. The keeping member and reference guide can be opened, unfolded, refolded, and closed with only one hand, even while wearing bulky gloves. The entire invention is made of flexible materials that are comfortable, durable, and safe to a person wearing the article and participating in a rigorous physical activity. The reference guide is typically a map.

19 Claims, 4 Drawing Sheets

U.S. PATENT DOCUMENTS

| | | | |
|---|---|---|---|
| 5,882,763 A | | 3/1999 | Perttunen |
| 5,884,338 A | * | 3/1999 | Golde .......................... 2/247 |
| 5,984,362 A | | 11/1999 | Christman |
| 6,007,895 A | * | 12/1999 | McDonald .................... 281/2 |
| 6,045,158 A | | 4/2000 | Bergstresser |
| 6,063,227 A | | 5/2000 | Raymond et al. |
| 6,103,332 A | * | 8/2000 | McDonald .................... 281/2 |
| 6,158,777 A | | 12/2000 | Twardosz |
| 6,189,933 B1 | | 2/2001 | Felderman |
| 6,227,424 B1 | * | 5/2001 | Roegner ..................... 224/219 |
| 6,354,985 B2 | | 3/2002 | Huber |
| 6,425,137 B1 | * | 7/2002 | Fakhrai ........................ 2/170 |

* cited by examiner

WEARABLE FOLDED MAP

CROSS REFERENCE TO RELATED APPLICATIONS

This application claims the benefit of Provisional Patent application No. 60/303,356 filed Jul. 06, 2001, which is hereby incorporated by reference.

BACKGROUND—FIELD OF INVENTION

This invention relates generally to large, single sheet reference guides and more specifically to two or three dimensional maps that can be worn on the outside surface of a person's clothes.

BACKGROUND OF THE INVENTION

There are several problems with maps related to outdoor activities and more specifically to ski maps that are given away for free at ski resorts:

They are made of thin paper that easily tears, especially in snow and wind.

They are large maps, usually over 110 square inches, with several fold lines that also cause them to tear easily.

They must be stored in the pockets of ski pants or coats. A skier must remove one or both gloves in order to retrieve the map, unfold it, refold it, and put it away for temporary storage. Removal of gloves can be painful and can even be dangerous in certain weather conditions.

Several previous patents have attempted to fix these problems.

U.S. Pat. No. 4,957,310 attempts to overcome the problems mentioned herein by using a weather resistant map that completely encircles the skier's arm. The map may be folded in one dimension, yet it still encircles the arm. In order to view this map, a skier must first slide the map from the upper arm to the lower arm. The skier then unwraps the map from around the arm. Finally, the skier removes the entire map from the arm and holds the map with both hands. There are three disadvantages associated with this design. The first disadvantage is that the skier must manipulate the map with both hands in order to view any significant portion of the map. Using both hands can be difficult when trying to hold ski poles. The second disadvantage is that the map does not fit securely to the upper or lower arm because the map must easily slide to a position where the skier can unwrap the map. The skier cannot easily tighten the looped strap because the looped strap is inaccessible when the map is wrapped around the arm. The third disadvantage is that the flexible unfolded map becomes rigid when wrapped around the arm. This rigidity is caused by the cylindrical shape of the folded map, which now restricts the flexibility of the map in almost all dimensions. This rigidity is a problem when the map slides to the skier's elbow and the skier consequently has difficulty bending the elbow.

U S. Pat. No. 5,400,936 and U S. Pat. No. 5,80,98 attempt to solve the general map problems listed previously by using 'map pouches' which allow traditional ski maps to be inserted into transparent, weather-resistant pouches. The primary disadvantage with these designs is that the maps are still difficult to read and manipulate. The portion of the map that can be visible at any one time is quite small, usually nine square inches or less, because the map must be folded in order to fit in the pouch. To see other parts of the ski map, the skier must remove the map from the pouch, re-fold it so that the desired portion of the map is visible, and then replace the map in the pouch. Removing and folding the map usually requires that the skier remove his or her gloves.

U.S. Pat. No. 5,743,449 uses a weather resistant ski map that is worn around the neck. There are two disadvantages associated with this design. The first disadvantage with this design is that the map is not attached securely to the body if it is worn on the outside of the ski jacket. The map can move about when the skier is skiing at a high velocity or in windy conditions. In either situation, the skier's visibility could easily be impaired. The second disadvantage with this design is that if the map is temporarily stored inside a ski jacket, the skier must remove his or her gloves to unzip the ski jacket and retrieve the map. As stated previously, it is undesirable to remove ski gloves or mittens at any time on the mountain.

Two of the aforementioned problems are also prevalent in other outdoor maps and the activities associated with these maps. For example, maps for hiking trails are usually so large and unwieldy that they easily tear. In these outdoor activities, it is also beneficial to be able to open, manipulate, and close a map with only one hand.

SUMMARY OF THE INVENTION

The objectives of this invention are to allow large size maps or reference guides to be worn externally on a person's body such that:

(a) gloves or mittens do not have to be removed in order to manipulate the map, (b) a person can easily manipulate the map with only one hand—even while wearing gloves, (c) the map can be attached securely to the human body while not interfering with any rigorous physical activity such as snow skiing, (d) the map is easily legible for even large areas of land, (e) the map is resistant to tearing, snow, ice, rain, and wind, and (f) one or more straps can be easily adjusted while wearing the map on the arm, torso, or leg.

In general, the invention is a foldable, weather-resistant map that is worn on a person's forearm, although the map could be worn on the upper arm, torso, or thigh. The map is folded into a small size, for example, less than 11 square inches, when not in use. The map unfolds to a full-size or slightly reduced-size map, for example, more than 100 square inches and less than 400 square inches. The map, when unfolded, is substantially flat. When folded, the map is also substantially flat but slightly thicker than when unfolded. The map can be held in the folded position via the use of a soft case, which serves as a keeping member. Alternatively, the map can be held in the folded position via the use of a fastening means such as hook & loop fasteners, snaps, or other similar means on the inner or outer surfaces of the folded map. The map can be folded several times in order to fold-up into a small compact size that is not intrusive to a person participating in a rigorous physical activity such as snow skiing.

The map can be attached to the keeping member either permanently via the use of adhesives or stitching or temporarily via the use of hook & loop fasteners or snaps. The soft case or keeping member is generally attached to one or more looped straps that encircles the arm, torso, or leg. The soft case can be attached to the looped strap or straps either permanently or temporarily. Alternatively, the looped strap or straps can be part of the soft case or keeping member.

However, the folded map itself does not encircle the arm, torso, or leg. The folded map and keeping member form a substantially flat surface that conforms to a skier's arm, torso, or leg such that the map and keeping member are not intrusive when snow skiing or when participating in other outdoor activities. If a soft case is not used, the map can be attached directly to the looped strap via a permanent attachment means such as glue or stitching, or the map could be attached temporarily to the looped strap via hook & loop fasteners or snaps.

The looped strap can be made of a flexible material such as elastic, nylon, or some other fibrous material. The looped strap can be adjustable by means of an elastic type material, a loop attachment with hook & loop fasteners, or a buckle type attachment. Thus, persons of various sizes can utilize the same size map, and one can move the map up, down, and around the upper arm or forearm so that the map is not intrusive when skiing or participating in other outdoor activities.

The map is made weather-resistant by printing the map directly on a weather-resistant material such as a synthetic fiber paper or with the use of laminates. The map may contain additional or different printed information such as instructional guides, safety warnings, advertisements, or other reference material.

DESCRIPTION OF THE PREFERRED EMBODIMENT

Figure 1:
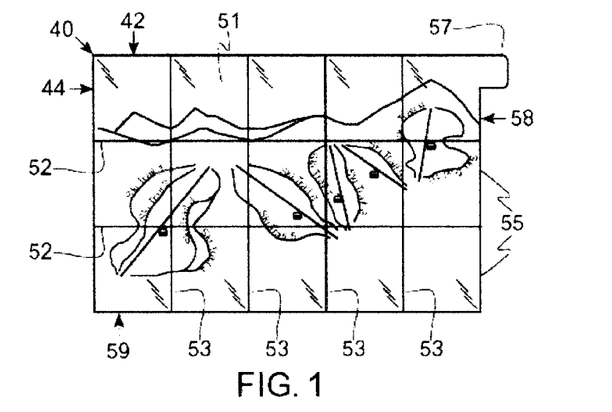
FIG. 1 is a top view of the preferred embodiment of the substrate in an unfolded configuration.
Figure 2:
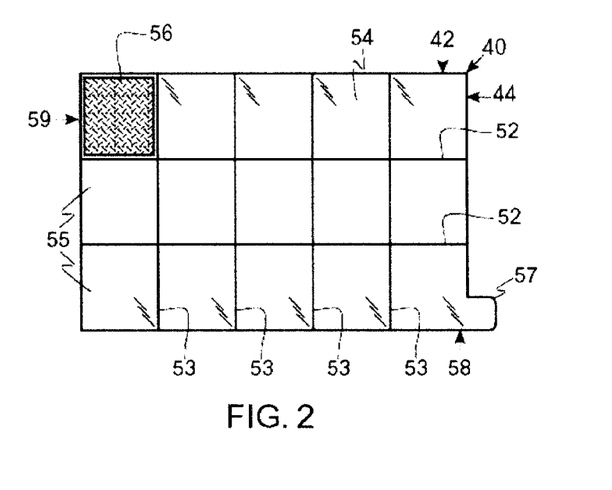
FIG. 2 is a bottom view of the preferred embodiment of the substrate in an unfolded configuration.

A substrate 40 is shown in FIGS. 1–2 in an unfolded configuration. The substrate 40 is a rectangular, substantially planar structure, having a front surface 51 shown in FIG. 1 and having a back surface 54 shown in FIG. 2. As a rectangular planar structure, the substrate 40 has horizontally extending edges 42 and vertically extending edges 44 as shown in FIGS. 1–2.

Figure 3:
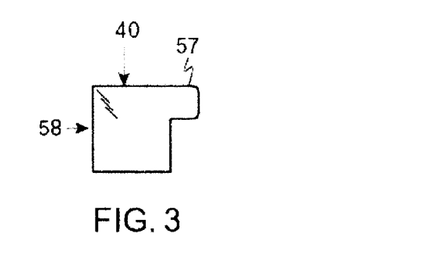
FIG. 3 is a top view of the preferred embodiment of the substrate in a folded configuration.
Figures 4, 5:
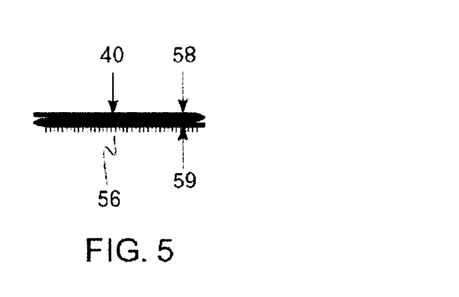
FIG. 4 is a bottom view of the preferred embodiment of the substrate in a folded configuration.
FIG. 5 is a side view of the preferred embodiment of the substrate in a folded configuration.

As shown in FIGS. 1–2, the substrate 40 includes one or more horizontal fold lines 52 located intermediate the horizontally extending edges 42 whereby the substrate may be folded once or more onto itself. The substrate 40 also includes one or more vertical fold lines 53 located intermediate the vertically extending edges 44 whereby the substrate may be folded once or more onto itself. With the combination of horizontal and vertical fold lines 52 and 53, the substrate 40 folds into a significantly smaller configuration as shown in FIGS. 3–5. The horizontal and vertical fold lines 52 and 53 divide the substrate 40 into approximately equivalent size substrate panels 55. As shown in FIGS. 1–2, a first corner panel 58 is located diagonally opposite a second corner panel 59.

A folded configuration of the preferred embodiment of the substrate 40 is shown in FIGS. 3–5 as a substantially rectangular structure, which is significantly smaller, but thicker, than the unfolded configuration shown in FIGS. 1–2. In the folded configuration, the substrate 40 can be stored in a significantly smaller, more compact size that is non-intrusive to a person participating in a moderate or rigorous physical activity. In the unfolded configuration, a person can view any information printed on either surface of the substrate 40.

The substrate 40 is stored in the folded configuration via the use of a keeping member 60. The keeping member 60 is shown in FIGS. 6–9. The keeping member 60 is comprised of a keeping member base 61 and a keeping member lid 62. In the preferred embodiment, the keeping member base 61 and the keeping member lid 62 are attached to one another as one continuous material. In other embodiments, the keeping member base 61 and the keeping member lid 62 could be attached via a hinge. The keeping member 60 is made of a material that conforms easily to a person's arm, leg, or torso. In the preferred embodiment, the keeping member material is a completely flexible material such as the cloth used for outdoor backpacks or nylon luggage. In other embodiments, the keeping member material could be a soft, flexible plastic that can withstand the temperature and moisture extremes of winter skiing conditions. By utilizing a soft, flexible keeping member, the invention will remain comfortable, durable, and safe to a person participating in moderate or physical activities.

Figure 6:
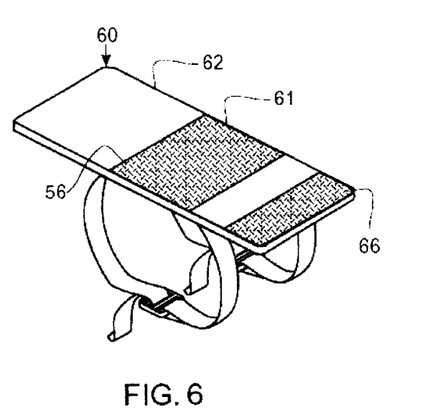
FIG. 6 is a perspective view of the top of the preferred embodiment of the keeping member in an open configuration without the substrate.
Figure 7:
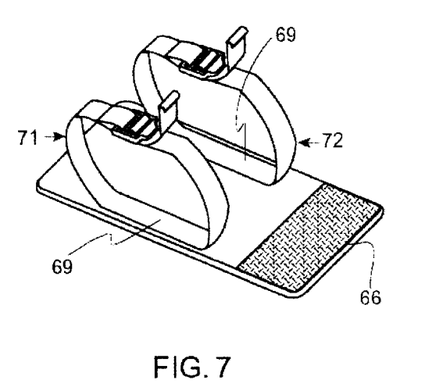
FIG. 7 is a perspective view of the bottom view of the preferred embodiment of the keeping member in an open configuration.
Figure 8:
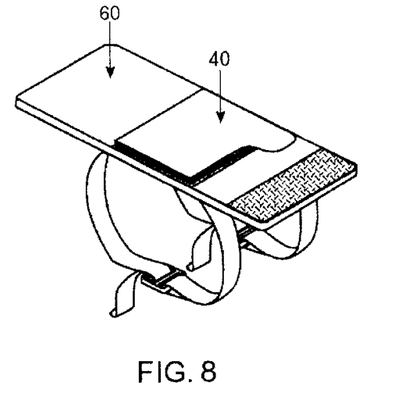
FIG. 8 is a perspective view of the top of the preferred embodiment of the substrate in a folded configuration and the keeping member in an open configuration.

The keeping member 60 is shown in an open configuration in FIGS. 6–8. With the keeping member 60 in an open configuration, a person can access the substrate 40 as shown in FIG. 8. The keeping member 60 is shown in a closed configuration in FIG. 9. With the keeping member 60 in a closed configuration, the substrate 40 is stored in a folded configuration and remains safe and non-intrusive to a person utilizing the invention while participating in moderate or rigorous physical activities.

The keeping member 60 is held in the closed configuration via the use of a keeping member fastener 66. In the preferred embodiment, the keeping member fastener 66 is implemented as mating hook & loop fasteners and these hook & loop fasteners are located on the keeping member 60 as shown in FIGS. 6–7. The keeping member 60 is held closed via the mating of these hook & loop fasteners. In other embodiments, other fastening implementations can be used such as male & female snaps, frictional fasteners, or magnetic fasteners.

Figure 9:
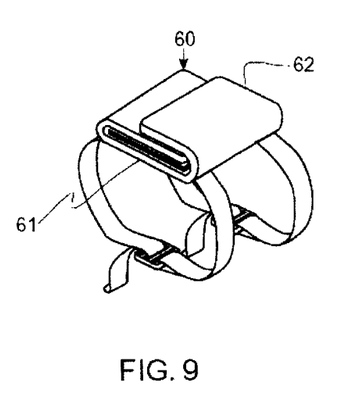
FIG. 9 is a perspective view of the preferred embodiment of the substrate in a folded configuration and the keeping member in a closed configuration

In the preferred embodiment and as shown in FIG. 9, the keeping member lid 62 extends above the keeping member base 61 while the keeping member 60 is in the closed configuration such that a person can easily grasp the keeping member lid 62 with only one hand, even while wearing bulky gloves. By grasping the keeping member lid 62, a person can easily open the keeping member 60 in order to gain access to the substrate 40. In other embodiments, one or more keeper opening means may be implemented as tabs that extend past the perimeter of the keeping member 60 to assist a person trying to open the keeping member 60. These tabs may be integrally connected to the keeping member 60, may be of a different material than the keeping member 60, or may be located in other locations to enable a person to more easily open the keeping member 60.

The substrate 40 is attached to the keeping member 60 via the use of a substrate attachment member 56. In the preferred embodiment, the substrate attachment member 56 is implemented as mating hook & loop fasteners located on the back surface 55 of the second corner panel 59 and on the top surface of the keeping member base 61. The substrate attachment member 56 is shown in FIGS. 2,4,5, and 6. The substrate 40 is secured to the keeping member 60 via the mating of these hook & loop fasteners as shown in FIG. 8. In other embodiments, the substrate 40 could be attached to the keeping member 60 with permanent attachment means such as glue, adhesives, or thread. Alternatively, the substrate 40 could be attached to the keeping member 60 with temporary attachment means such as snaps, magnetic devices, or other frictional devices.

An unfolding member 57 is located on the perimeter of the substrate 40 as shown in FIGS. 1–4. In the preferred embodiment, the unfolding member 57 is a tab located on the first corner panel 58 as shown in FIG. 2. The unfolding member 57 allows a person wearing gloves to more easily unfold the substrate 40 by allowing the person to grasp a portion of the substrate that extends past the perimeter of the folded substrate 40 as shown in FIGS. 3–4. In the preferred embodiment, the unfolding member 57 is an extension of the substrate 40. In other embodiments, the unfolding member 57 may be located on other substrate panels 55 or it may be made of a separate material than the substrate 40.

As shown in FIGS. 1–5, the horizontal fold lines 52 and vertical fold lines 53 allow the substrate 40 to be folded into a rectangular configuration. In other embodiments, the fold lines 52 and 53 may not be straight lines, the fold lines 52 and 53 may not be at right angles to one another, or additional fold lines may be present to allow a large substrate to be folded into a smaller, non-rectangular, substantially planar structure.

In the preferred embodiment, an even number of the horizontal and vertical fold lines 52 and 53 yields an odd number of substrate panels 55. When the substrate 40 is folded in an accordion style fold across both the horizontal and vertical fold lines 52 and 53, the first corner panel 58 is on an outer surface of the folded substrate 40 while the opposite surface of the folded substrate 40 is the second corner panel 59 which is attached to the keeping member 60.

The combination of an odd number of substrate panels 55 and an accordion style fold technique enables a person to unfold and refold the substrate 40 with one hand, even while wearing bulky gloves because the second corner panel 59 is attached to the keeping member 60. In other embodiments, an even number of substrate panels 55 and non-accordion fold techniques may be implemented, although these other embodiments can make it more difficult for a person to unfold and refold the substrate 40.

A first looped strap 71 and second looped strap 72, shown in FIGS. 6–9, are attached to the bottom surface of the keeping member base 61 in order to secure the keeping member 60 to a person's arm, torso, or leg. A looped strap attachment member 69 secures looped straps 71 and 72 to keeping member 60. In the pictured embodiment, the looped strap attachment member is implemented as a permanent attachment means such that the looped straps 71 and 72 are stitched to the keeping member base 61 with thread. In other embodiments, the looped strap attachment member 69 could be implemented as other forms of permanent or temporary attachment means such as glues, adhesives, snaps, clamps, belt loops, hook & loop fasteners, rivets, or solder.

In the preferred embodiment, the first and second looped straps 71 and 72 are implemented as elastic cloth strips with buckle fasteners. Other implementations of a looped strap may be used such as elastic cords, elastic bands, rope, twine, hook & loop fasteners, or other means so as to allow a person to adjust the looped strap while it is worn on a person's arm, torso, or leg. In other configurations, one or more looped straps may be used to secure the invention to a person's body. Additionally, the looped strap 71 could be implemented as a continuous material of the keeping member 60. In another configuration, the looped strap 71 could be a belt worn around the waist, a strap on a backpack, or a strap on a waist pack. In still another configuration, the looped strap 71 could secure the keeping member 60 to the handlebars or steering mechanism of a bicycle, motorcycle, snowmobile, or other motorized or non-motorized vehicle.

In the preferred embodiment, the looped strap attachment member 69, first looped strap 71, and second looped strap 72 are made of flexible materials such as cloth and thread. By using flexible materials, the first and second looped straps 71 and 72 and the looped strap attachment member 69 remain comfortable, durable, and are safe to a person wearing the invention while participating in a moderate or rigorous physical activity.

The small size of the folded configuration of the substrate 40 and the roughly equivalent size of the keeping member 60 ensures that the keeping member and the folded substrate 40:

a) only touches one side of a person's arm, torso, or leg,     b) does not extend significantly past the diameter of a person's arm, and     c) allows a person to have access to any adjustment means for one or more looped straps.

In the preferred embodiment, the substrate 40 and unfolding member 57 are made of a flexible material. A flexible material insures that the substrate 40 and unfolding member 57 do not become rigid when the substrate 40 is in the folded or unfolded configuration. By remaining flexible in the unfolded or folded configuration, the substrate 40 and unfolding member 57 will remain comfortable, durable, and safe when the invention is used in rigorous or moderate physical activities.

The preferred substrate material is a high quality, photographic, synthetic fiber paper or plastic that is printable on at least one side, preferably both sides. The synthetic fiber paper is protected from snow, ice, rain, and wind, or an additional coating can be applied to allow the same protections.

In the preferred embodiment, a map is printed on at least one surface of the substrate 40. In other embodiments, other visual information such as instructional guides, safety procedures, advertisements, or other reference material may be printed on at least one surface of the substrate 40.

In the preferred embodiment, the entire invention is made of flexible materials, which enables the invention to be comfortable, durable, and safe to a person wearing the invention and participating in a rigorous physical activity.

In operation of the preferred embodiment, a person attaches the substrate 40 to the keeping member 60 as shown in FIG. 8. FIGS. 11–14 illustrate a manner in which the person may open the keeping member 60 and unfold the substrate 40. With the keeping member 60 on the forearm as shown in FIGS. 10–11, the person unfastens the keeping member fastener 66 and then opens the keeping member 60 by rotating the keeping member lid 62 away from the keeping member base 61.

Figure 12:
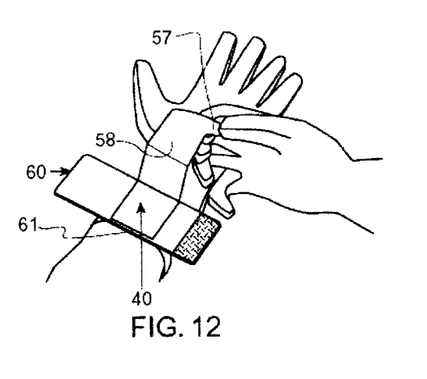
FIG. 12 is a perspective view of the preferred embodiment showing the next step of a person unfolding the substrate.
Figure 13:
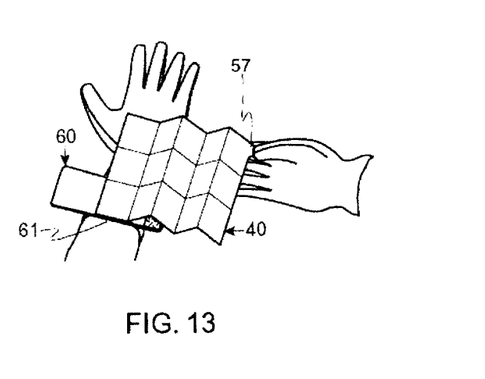
FIG. 13 is a perspective view of the preferred embodiment showing an intermediate step of a person unfolding the substrate.
Figure 14:
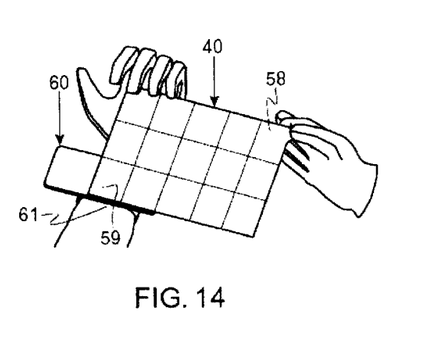
FIG. 14 is a perspective view of the preferred embodiment of the substrate in the final, unfolded state.

In FIG. 12, the person, with bare hands or while wearing his or her gloves or mittens, grasps the unfolding member 57 in order to pull the first corner panel 58 away from the second corner panel 59 while the second corner panel 59 is attached to the keeping member base 61. The person pulls the unfolding member 57 completely away from the keeping member base 61 as shown in FIGS. 12–14.

To refold and secure the substrate 40 in the keeping member 60, the person simply reverses the preceding steps. To secure the keeping member 60 in the closed position, the person presses the mating hook & loop fasteners of the keeping member fastener 66 together until they are securely coupled.

Figure 10:
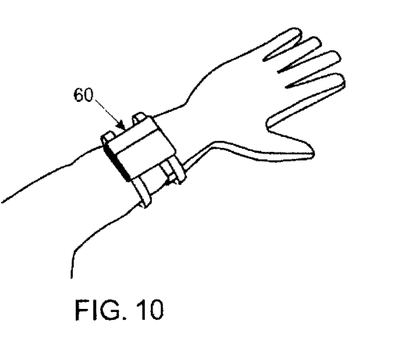
FIG. 10 is a perspective view of the preferred embodiment of the substrate in a folded configuration, the keeping member in a closed configuration, and the looped straps encircling a person's arm.
Figure 11:
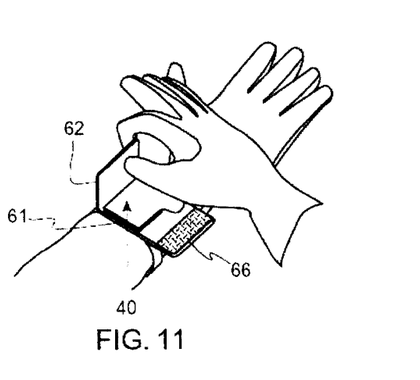
FIG. 11 is a perspective view of the preferred embodiment showing the first step of a person opening the keeping member.
Figure 15:
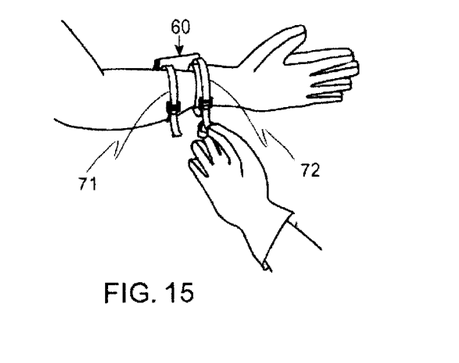
FIG. 15 is a perspective view of the preferred embodiment showing a person adjusting a looped strap.

In FIG. 10, which illustrates the substrate 40 in the folded configuration and the keeping member 60 in the closed configuration, the keeping member is essentially tangent to a small portion of the looped strap 71, and the keeping member does not encircle the person's arm. With the keeping member 60 attached securely to the person's arm, he or she is able to easily adjust any looped straps without moving the entire keeping member from the arm as shown in FIG. 15. This adjustment mechanism allows a person to move the keeping member 60 up, down, and around the arm so that the keeping member is not intrusive during to a person participating in a rigorous activity such as snow skiing. These advantages extend to other embodiments where the keeping member 60 is worn on the torso, leg, a belt, a backpack strap, and in situations where the invention is used for other rigorous outdoor activities.

Figure 16:
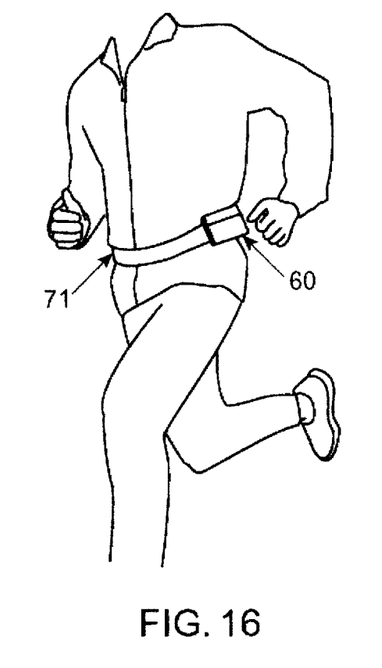
FIG. 16 is a perspective view of the perferred embodiment showing the keeping member attached to a looped strap that encircles a person±torso.
Figure 17:
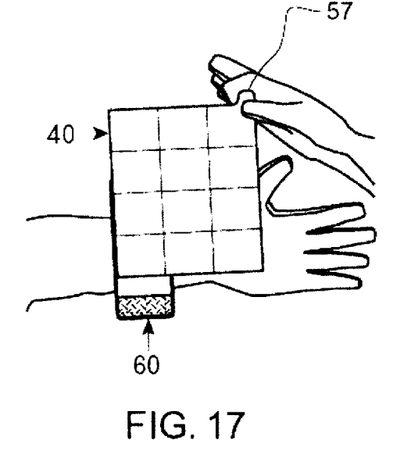
FIG. 17 is a perspective view of a user rotating the map substrate in order to see the opposite side of the map substrate.

FIG. 16 is an illustration of the preferred embodiment being worn on the torso.

Conclusion, Ramifications, and Scope

The preferred embodiment described herein may take other forms such as the location of the substrate attachment member 56, unfolding member 57, and horizontal and vertical fold lines 52 and 53 such that the substrate 40 folds into a different rectangular configuration or opens and closes in a different sequence. One or more tabs or keeper opening means may be located on the keeping member 60 to assist in the opening and closing of the keeping member while a person is wearing gloves. A hinge may be present to connect the keeping member base 61 to the keeping member lid 62. The keeping member fastener 66 may take other forms such that the keeping member 60 opens and closes in a different sequence or is secured shut with a different mechanism. The keeping member 60 may or may not completely enclose the folded substrate 40 due to the size of the unfolding member 57. The looped strap attachment member 69 could be located anywhere on the keeping member 60 or it could be attached directly to the substrate 40.

The invention could be implemented with person attachment means other than a looped strap whereby the keeping member 60 is secured to a person's torso, leg, belt, backpack, or waist pack. In addition, the keeping member 60 could hold additional items such as a ski lift ticket, season pass, cash, or credit cards.

The substrate 40 could have visual information other than a map depicted thereon.

The combination of the substrate 40 with an odd number of substrate panels 55, an accordion fold technique, the first corner panel 58 containing the unfolding member 57 located diagonally opposite to the second corner panel 59 allows a person to unfold the substrate 40 with only one hand when the substrate 40 is attached to the keeping member 60. When a looped strap is attached to a person's arm, a person can open the keeping member 60, unfold and refold the substrate 40, and close the keeping member with only one hand, even while wearing bulky gloves. By utilizing flexible materials, the entire invention is comfortable, durable, non-intrusive, and safe to a person participating in a rigorous physical activity It should be appreciated that the invention described herein is well adapted to perform the objects set forth above.

I claim:

1. A wearable reference guide comprising:
    a. a flexible, substantially flat substrate having front and back surfaces, at least one surface having printed visual information depicted thereon, said substrate being foldable into a substantially flat configuration;
    b wherein said substrate has opposed horizontally extending edges and is foldable along at least one horizontal fold line intermediate the edges;
    c. wherein said substrate has opposed vertically extending edges and is foldable along at least one vertical fold line intermediate the edges;
    d. wherein said substrate includes a plurality of panels each bounded by two of the said horizontal fold lines, vertical fold lines, horizontally extending edges, and vertically extending edges;
    e. wherein said substrate contains an unfolding member on at least one of the said panels;
    f. a flexible keeping member that keeps said substrate in a folded configuration;
    g. a keeping member fastener that secures said keeping member in a closed configuration;
    h. a flexible looped strap attachment member that connects said keeping member to one or more looped straps;
    i. a substrate attachment member that secures said substrate directly to said keeping member such that said substrate can be completely unfolded and folded with only one hand while substrate is attached directly to said keeping member and while said keeping member is in an open configuration and while keeping member is attached to a person via one or more looped straps.

2. The wearable reference guide of claim 1, wherein said printed information on at least one of said substrate surfaces is a map.

3. The wearable reference guide of claim 1, wherein said substrate attachment member is a mating hook & loop fastener.

4. The wearable reference guide of claim 1, wherein said looped strap attachment member connects said keeping member to a looped strap that encircles a person's arm.

5. The wearable reference guide of claim 1, wherein said looped strap attachment member connects said keeping member to a looped strap that encircles a person's torso.

6. The wearable reference guide of claim 1, wherein said keeping member is incorporated directly into an article of clothing.

7. The wearable reference guide of claim 1, wherein said keeping member does not encircle a person's arm.

8. The wearable reference guide of claim 1, wherein said keeping member encircles a person's arm such that a looped strap is an integral part of said keeping member.

9. The wearable reference guide of claim 1, wherein said unfolding member is located on a first corner panel of said substrate located diagonally opposite to a second corner panel of said substrate wherein the second corner panel further contains said substrate attachment member.

10. The wearable reference guide of claim 1, wherein said unfolding member is a tab that extends past a perimeter of said substrate when the substrate is in a folded configuration.

11. The wearable reference guide of claim 1, wherein said unfolding member is located on the outermost panel when said substrate is in a folded configuration and kept in said keeping member.

12. The wearable reference guide of claim 1, wherein said horizontal fold lines and vertical folds lines yields an odd number of said panels.

13. The wearable reference guide of claim 1, wherein said foldable substrate is folded in an accordion style fold pattern across said horizontal fold lines and across said vertical fold lines.

14. The wearable reference guide of claim 1, wherein said keeping member further comprises a keeper opening means for opening and closing said keeping member in order for a person to gain access to substrate.

15. The wearable reference guide of claim 1, wherein said keeping member can be opened and closed with only one gloved hand when said keeping member is attached to a person's body via at least one looped strap.

16. The wearable reference guide of claim 1, wherein both sides of said substrate can be easily viewable with only one hand while said substrate is unfolded and while said substrate is attached to said keeping member when the keeping member is attached to a person's arm via at least one looped strap.

17. The wearable reference guide of claim 1, wherein said substrate is coated with a transparent, resilient material in order to make the substrate resistant to snow, water, ice, or wind.

18. The wearable reference guide of claim 1, wherein said substrate is made of a synthetic fiber paper that is resistant to tearing, snow, water, ice, or wind.

19. A wearable reference guide comprising:
   i. a flexible, substantially flat substrate having front and back surfaces, at least one surface having printed visual information depicted thereon, said substrate being foldable into a substantially flat configuration;
   j. wherein said substrate has opposed horizontally extending edges and is foldable along at least one horizontal fold line intermediate the edges;
   k. wherein said substrate has opposed vertically extending edges and is foldable along at least one vertical fold line intermediate the edges;
   l. wherein said substrate includes a plurality of panels each bounded by two of the said horizontal fold lines, vertical fold lines, horizontally extending edges, and vertically extending edges;
   m. wherein at least one panel of said substrate further comprises an unfolding member;
   n. a flexible keeping member that keeps said substrate in a folded configuration;
   o. a keeping member fastener that secures said keeping member in a closed configuration;
   p. a flexible looped strap attachment member that connects said keeping member to one or more looped straps;
   q. a substrate attachment member that secures said substrate directly to said keeping member such that said substrate can be completely unfolded and folded with only one hand while substrate is attached directly to said keeping member and while said keeping member is in an open configuration and while keeping member is attached to a person via one or more looped straps;
   r. wherein both sides of said substrate can be easily viewable with only one hand while said substrate is unfolded and while said substrate is attached to said keeping member when the keeping member is attached to a person's arm via at least one looped strap.

* * * * *